United States Patent [19]

March et al.

[11] Patent Number: 5,306,250
[45] Date of Patent: Apr. 26, 1994

[54] METHOD AND APPARATUS FOR INTRAVASCULAR DRUG DELIVERY

[75] Inventors: Keith L. March, Carmel; David R. Hathaway, Indianapolis; Robert L. Wilensky, Carmel, all of Ind.

[73] Assignee: Indiana University Foundation, Bloomington, Ind.

[21] Appl. No.: 862,075

[22] Filed: Apr. 2, 1992

[51] Int. Cl.⁵ ............................ A61M 29/00
[52] U.S. Cl. ................................... 604/104
[58] Field of Search ............... 604/96, 104, 107, 108, 604/53, 28, 48, 49, 54, 93, 265, 266, 269; 606/191, 198

[56] References Cited

U.S. PATENT DOCUMENTS

| | | | |
|---|---|---|---|
| 638,367 | 12/1899 | Tuttle . | |
| 2,499,045 | 8/1948 | Walker et al. | 128/261 |
| 3,173,418 | 3/1965 | Baran | 128/351 |
| 3,394,705 | 7/1968 | Abramson | 128/349 |
| 3,701,351 | 10/1972 | Harvey | 128/260 |
| 4,364,392 | 12/1982 | Strother et al. | 128/325 |
| 4,423,725 | 1/1984 | Baran et al. | 128/207.15 |
| 4,437,856 | 3/1984 | Valli | 604/29 |
| 4,515,587 | 5/1985 | Schitt | 604/96 |
| 4,573,966 | 3/1986 | Weikl et al. | 604/53 |
| 4,650,466 | 3/1987 | Luther | 604/95 |
| 4,655,748 | 4/1987 | Mushika | 604/96 |
| 4,773,899 | 9/1988 | Spears | 604/20 |
| 4,785,815 | 11/1988 | Cohen | 128/642 |
| 4,824,436 | 4/1989 | Wolinsky | 604/53 |
| 4,878,492 | 11/1989 | Sinofsky | 128/303.1 |
| 4,885,003 | 12/1989 | Hillstead | 604/107 |
| 4,976,711 | 12/1990 | Parins et al. | 606/48 |
| 4,994,033 | 2/1991 | Shockey et al. | 604/101 |
| 4,998,539 | 3/1991 | Delsanti | 128/898 |
| 5,002,560 | 3/1991 | Machold et al. | 606/198 |
| 5,041,093 | 8/1991 | Chu | 606/98 |
| 5,087,244 | 2/1992 | Wolinsky et al. | 604/53 |
| 5,171,217 | 12/1992 | March et al. | 604/53 |

FOREIGN PATENT DOCUMENTS

0383429A2  1/1990  European Pat. Off. .

*Primary Examiner*—C. Fred Rosenbaum
*Assistant Examiner*—Manuel Mendez
*Attorney, Agent, or Firm*—Baker & Daniels

[57] ABSTRACT

A drug delivery catheter assembly, including an expandable, porous outer membrane that is insertable into a blood vessel and positioned adjacent a stenotic atherosclerotic lesion on the interior wall of the blood vessel. The membrane is expanded into contact with the lesion, either mechanically or hydraulically. After the membrane is expanded, a drug-containing liquid is caused to flow into the membrane and through the pores in the membrane into contact with the lesion.

35 Claims, 3 Drawing Sheets

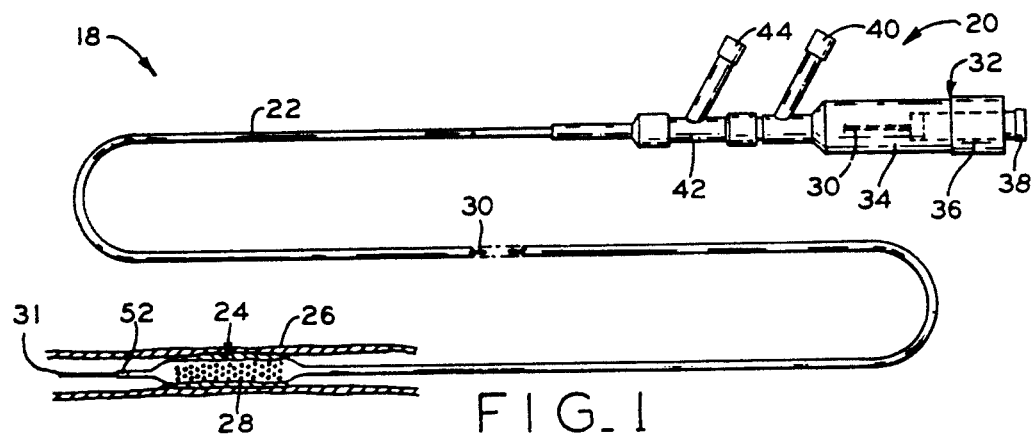
FIG_1
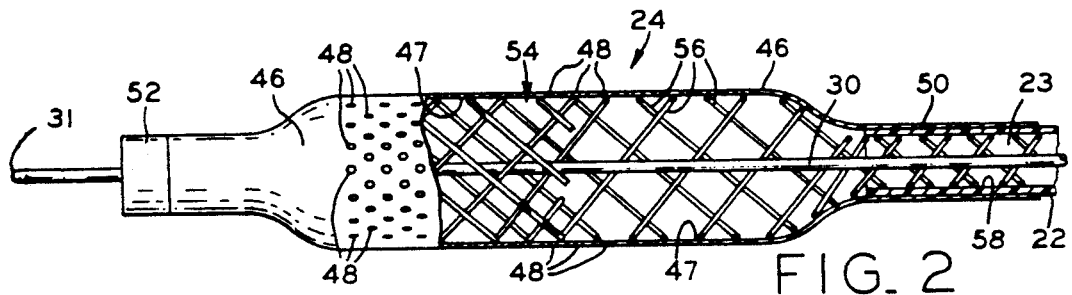
FIG_2
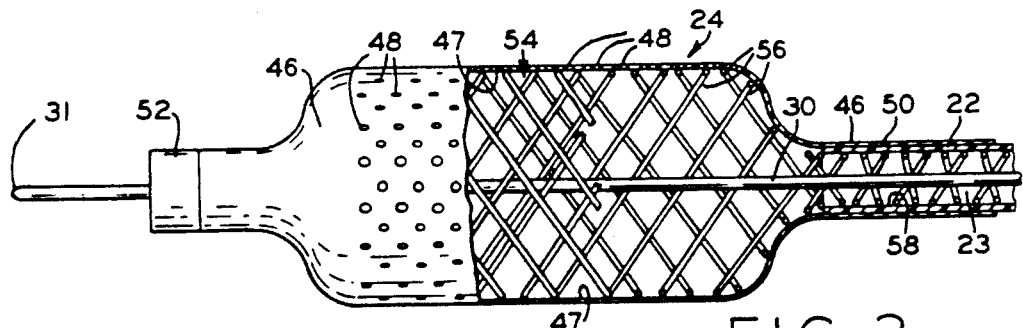
FIG_3
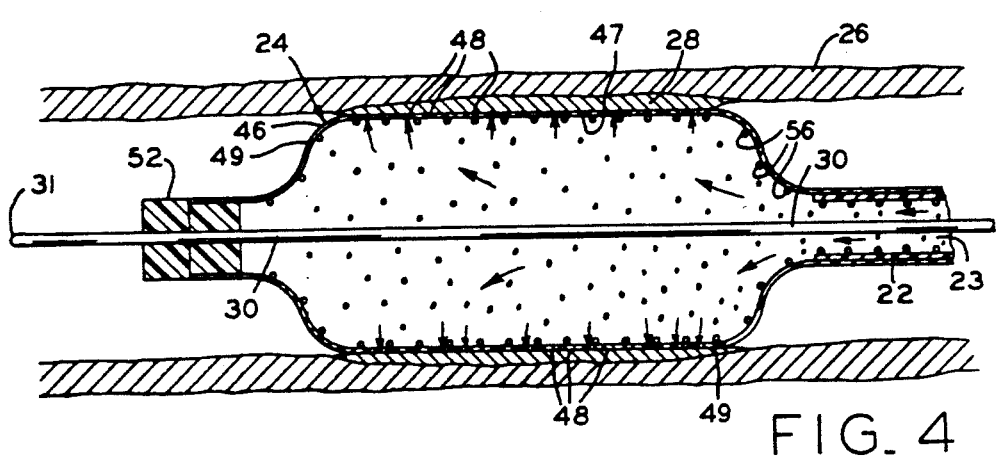
FIG_4

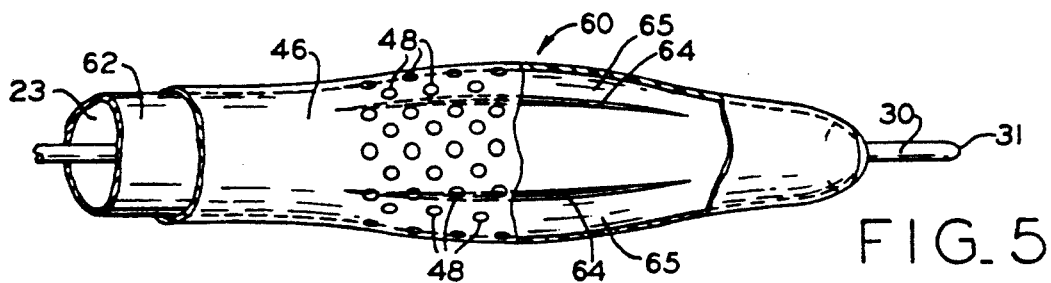
FIG_5
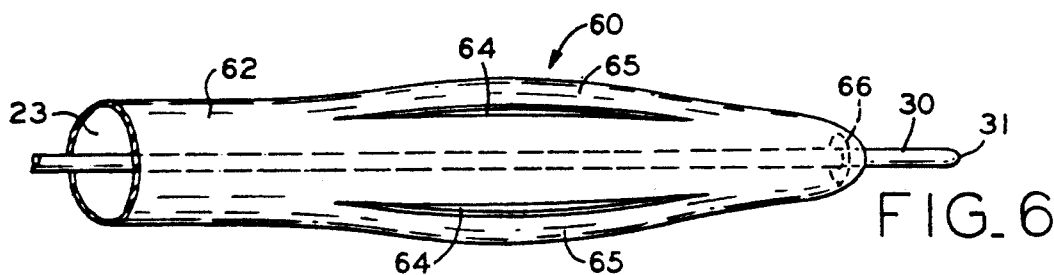
FIG_6
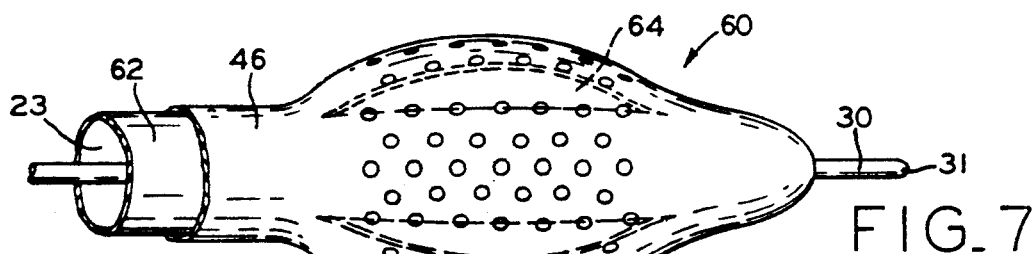
FIG_7
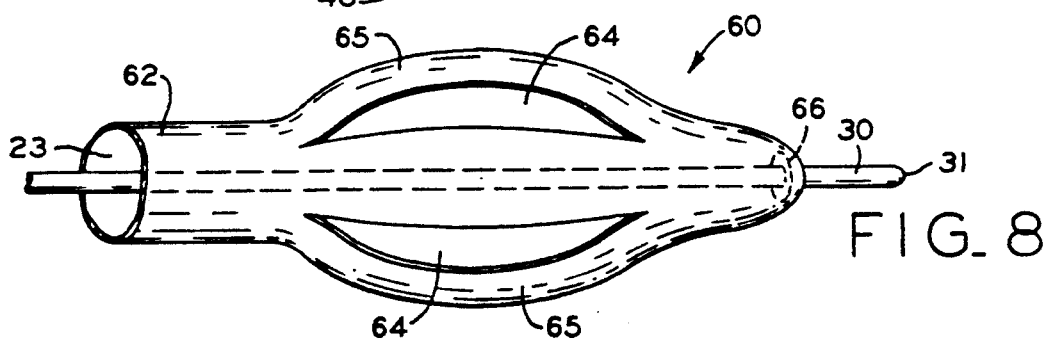
FIG_8
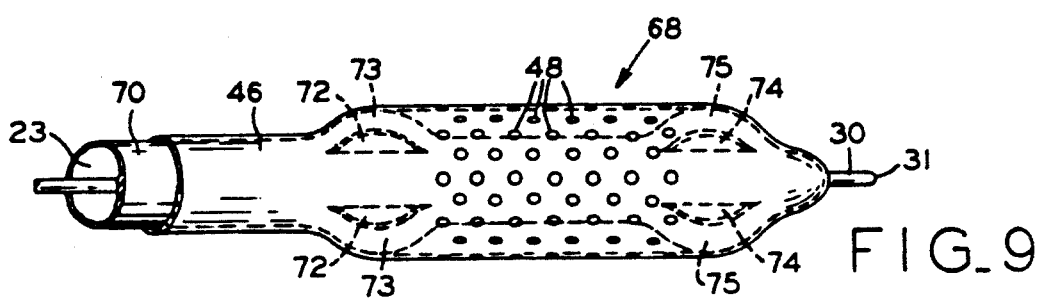
FIG_9

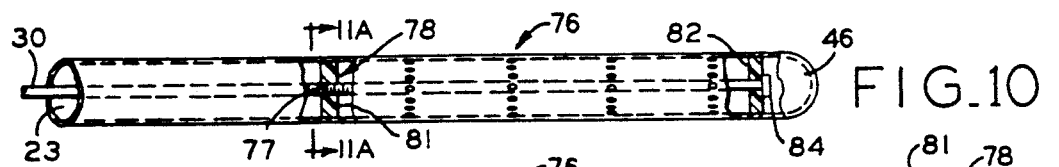
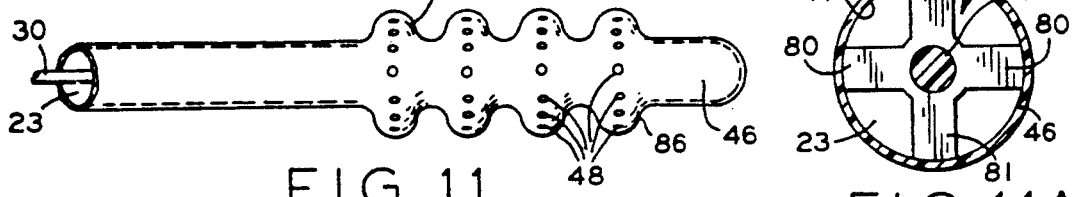
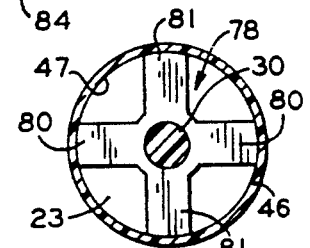
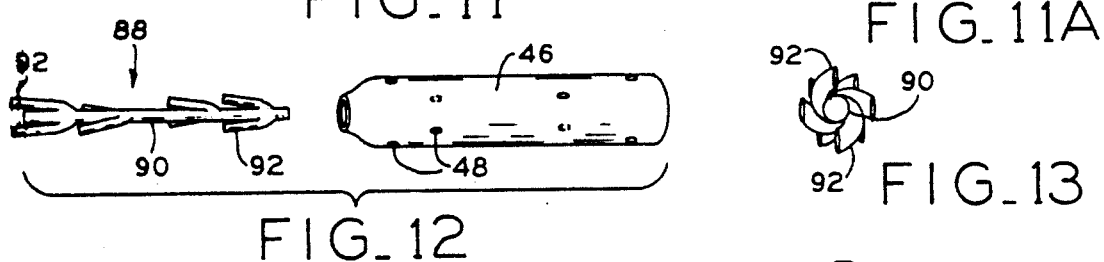
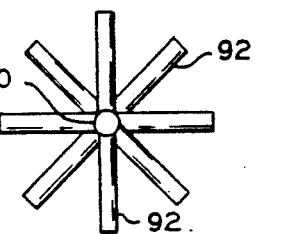
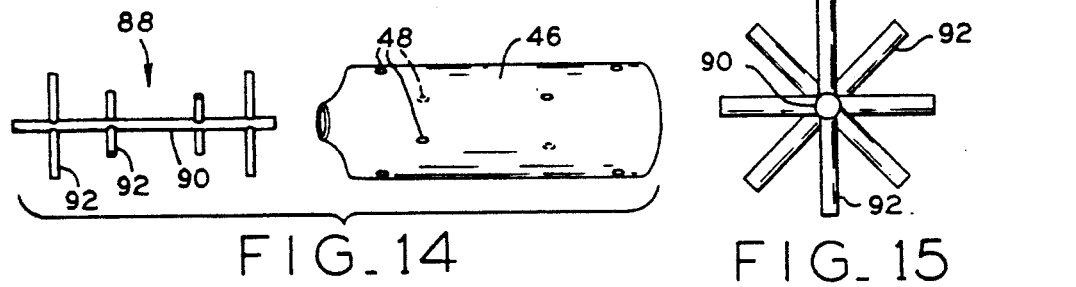
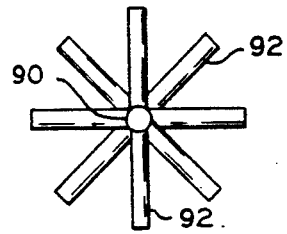
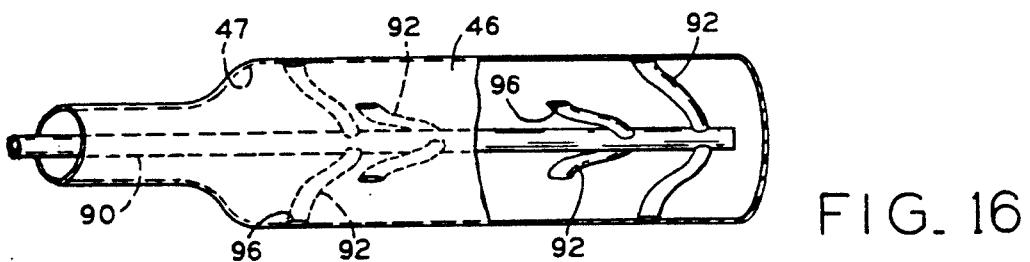
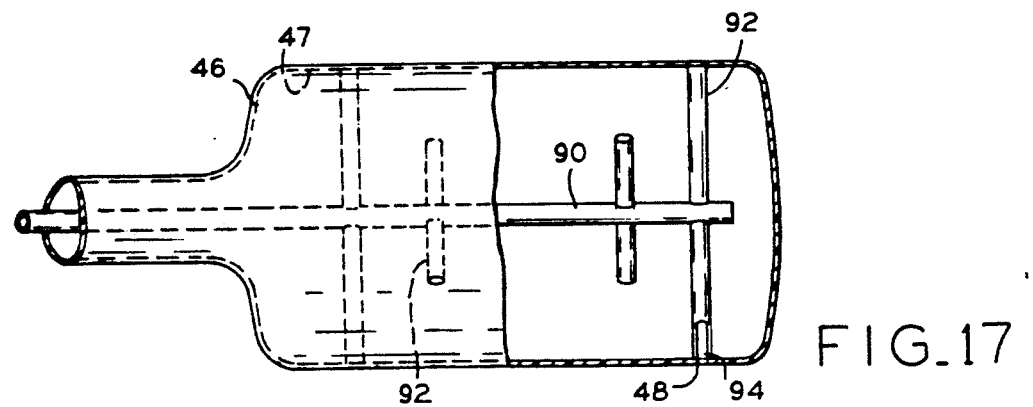

METHOD AND APPARATUS FOR INTRAVASCULAR DRUG DELIVERY

BACKGROUND OF THE INVENTION

The present invention relates to intravascular drug delivery devices which permit the administration of a drug directly to the inner wall of a tubular body vessel.

Percutaneous transluminal coronary angioplasty (PTCA) has been very effective for treating intravascular stenoses within coronary arteries and peripheral arteries. In this procedure a dilation catheter is advanced over a guide wire into the femoral or other access artery and advanced therein until the flexible, relatively inelastic balloon on the distal tip of the catheter is properly positioned within the stenotic vessel across the lesion to be dilated. The balloon is then inflated to a predetermined size with a radiopaque liquid at relatively high pressures to radially compress the stenotic lesion against the inside of the artery wall to thereby increase the luminal diameter of the stenotic vessel. The balloon is then deflated so that the dilation catheter can be removed and blood flow resumed through the stenotic vessel.

Although PTCA has proved to be an effective alternative to surgical intervention, the clinical results of angioplasty treatment include endothelial denudation, vascular wall damage, and rupture of the tunica intima vasorum. These injuries stimulate a number of growth processes, resulting in a high incidence of proliferation of arterial smooth muscle cells, with a resulting restenosis.

It is known that certain drugs, most notably heparin, are effective in reducing the reformation of certain types of stenotic lesions in animal models. Generally, these drugs show a tendency to inhibit smooth muscle cell proliferation. However, it is generally not desirable that these drugs be injected as a bolus dose to be carried to the site of the lesion, primarily due to the undesirable side effects caused by the relatively large dosage required. Therefore, it is desirable to administer these drugs directly to the lesion, so that a significantly smaller dosage may be employed and the side effects minimized.

One method for administering plaque-inhibiting drugs directly on stenotic lesions, disclosed in U.S. Pat. No. 4,824,436, issued to Wolinsky, utilizes a catheter having a main catheter body with a drug delivery conduit and a balloon expansion conduit therein. The catheter body is held in place by the inflation of two spaced balloons, one at the proximal end of the plaque body and the other at the distal end. The two balloons are inflated by forcing fluid through the balloon expansion conduit, thereby holding the catheter body in place and forming a drug-receiving chamber in the artery. Once the catheter is in place, a drug is forced through the central conduit and into the arterial chamber, whereupon the drug adheres to and penetrates the adjacent arterial tissue.

A problem with this arrangement is that the drug is administered through only a single opening in the catheter, so that the formation of a drug-receiving chamber is necessary to allow the drug to contact the entire lesion Burface. If the restenotic lesion occurs at a branched portion of a blood vessel, the balloons would be unable to form an enclosed chamber to prevent the drug from flowing downstream through the branched vessel.

A second device is disclosed in U.S. Pat. No. 4,994,033, issued to Shockey, et al. In this device, three elongated, flexible, delivery tubes are concentrically disposed relative to one another. Two expandable balloons or sleeves are located at the distal ends of the tubes. The outer drug delivery sleeve, which includes a pattern of micro-apertures therein, has its proximal end secured to the outer tube, and its distal end secured to the inner expander sleeve. The proximal end of the inner expander sleeve is attached to the intermediate tube, and the distal end is bonded to the innermost tube. Essentially, the drug is first introduced into the outer tube and into the drug delivery tube at a pressure generally insufficient to eject the drug out of the micro-apertures. Next, the inflation fluid is introduced through the intermediate tube and into the expander sleeve. As the pressure is increased within the expander sleeve causing it to expand, the drug is simultaneously forced through the micro-apertures to contact the lesion with the drug.

A problem with this catheter is that the outer sleeve cannot be expanded against the lesion absent an infusion pressure to the inner expander sleeve. Therefore, it would be difficult to control the amount of pressure exerted against the arterial wall. In addition, it would be difficult to control the amount of drug that is released through the micro-apertures, since the steps of balloon expansion and drug delivery occur simultaneously. In particular, there is opportunity for a significant loss of drug into the bloodstream both during injection of the drug into the outer sleeve and subsequent inflation of the inner sleeve, thereby causing expansion of the outer drug delivery sleeve that has already been injected with the drug. In addition, the interface between the inner and outer sleeves may cause resistance to injection of the drug through the micro-apertures upon inner sleeve expansion.

Yet another problem of the catheter device disclosed in Shockey, et al. is that an unequal distribution of drug is likely to occur upon delivering the drug to a stenotic lesion located at a branched arterial passageway. The distal end of the catheter positioned in the passageway has a low pressure side located toward the branched vessel and an opposite high pressure side. As the inner sleeve is expanded by the inflation fluid, drug is forced out through the micro-apertures in the outer sleeve. Since fluids take the path of least resistance, and since at least some of the drug is forced out of the outer sleeve during inflation of the expander sleeve, a significant amount of the drug is likely to be delivered out the low pressure side of the outer sleeve toward the branched vessel, leaving an insufficient supply of the drug delivered to the portion of the lesion adjacent the high pressure side of the outer sleeve.

A catheter having an expandable stent is disclosed in U.S. Pat. No. 5,002,560, issued to Machold, et al. The catheter assembly includes an expandable wire cage or stent that is formed by a plurality of spirally-arranged strands. The cage is radially expanded and contracted by a core member or guide wire that is disposed within an elongated catheter body. The proximal end of the assembly includes a manipulator, which includes an internally threaded cap and a torquing member. Rotation of the cap causes longitudinal movement of the externally threaded member, thereby moving the torquing member, which moves the guide wire attached thereto. Movement of the guide wire changes the axial spacing between the ends of the expandable cage, and thus the radial dimension of the cage.

This catheter assembly has performed effectively to maintain the patency of a blood vessel for a long period of time after a vascular procedure as well as to allow the perfusion of blood through the blood vessel while the blood vessel is held open. It is now desired to utilize some of these concepts in improving upon the drug delivery catheters of the prior art.

SUMMARY OF THE INVENTION

The present invention overcomes the problems of the above-described prior art by providing an inflatable drug delivery apparatus, and a method for using same, to apply a drug to a localized area of a tubular vessel, wherein an expandable, porous drug delivery membrane is inserted into a blood vessel adjacent the localized area to be treated, and the membrane is expanded into contact with the localized area before delivery of the drug through the pores. The apparatus includes a device for causing the liquid drug to flow into the membrane and out through the pores, wherein expansion of the membrane occurs independently of the flow of fluid through the pores in the membrane.

Generally, the present invention provides a catheter assembly for applying a liquid drug, or a drug dissolved or suspended in a liquid, to a localized area of a tubular body vessel, including a flexible drug delivery tube and an expandable, porous outer membrane connected to the tube at the distal end of the assembly for insertion into the tubular vessel adjacent the localized area. The membrane is expandable into contact with the localized area, wherein expansion of the membrane occurs independently of the delivery of drug into the membrane and out through the pores of the membrane.

More particularly, the present invention provides, in one form thereof, an endoskeletal frame within the membrane, wherein the frame exerts mechanical force on the membrane to expand the membrane before the drug is forced into and through the porous membrane. The endoskeletal frame is expanded by a retractable wire connected to the frame and mechanically actuated at the proximal end of the assembly. In one form, the endoskeletal frame may be an expandable wire mesh. In another form, the endoskeletal frame may be a tubular frame member having a plurality of slots therein to form a plurality of ribs, whereby the ribs expand radially when the wire is retracted.

In yet another form of the present invention, the porous sheet is pleated and is contractible axially to cause the pleated membrane to expand radially. In still another form of the invention, the membrane may be hydraulically expanded by a working fluid that is segregated from the liquid drug by a second inner tube, such that fluid is introduced through the inner tube to expand the outer membrane before drug is introduced through the pores in the membrane.

An advantage of the drug delivery apparatus of the present invention is that the porous membrane is expandable against the localized area of the blood vessel independent of drug delivery through the membrane, thereby permitting more accurate and controlled drug delivery.

A further advantage of the drug delivery apparatus of the present invention is that the drug may be effectively administered directly to the lesion while minimizing the loss of drug to the bloodstream, especially to those stenotic lesions located at branched vessels.

Yet another advantage of the drug delivery apparatus of the present invention is that drug may be delivered directly to a lesion without the accumulation of drug in an arterial chamber.

The present invention, in one form thereof, provides an apparatus for applying a drug to a localized area of a tubular body vessel. The apparatus includes an expandable, porous outer membrane and an elongate flexible tube connected to the membrane. A fluid delivery system is provided for pumping a drug-containing liquid through the tube into the membrane and through pores in the membrane. An expander is provided for expanding the membrane into contact with the vessel independent of the pumping of the liquid into and through the membrane.

The present invention further provides, in one form thereof, a method of treating a stenotic atherosclerotic lesion on the interior wall of a vessel, in which an expandable, porous outer membrane is inserted into the vessel adjacent the lesion. The membrane is expanded into contact with the lesion, and a drug-containing liquid is caused to flow under pressure into the membrane and through pores in the membrane into contact with the lesion. The expansion of the membrane occurs independently of the flow of pressurized drug-containing liquid into the membrane and through pores in the membrane.

The present invention, in one form thereof, provides an apparatus for drug delivery to other vessels and glands, such as the prostate, urethra, prostatic urethra, esophagus, fallopian tubes, rectum, intestine, bronchi, and pancreatic and gall bladder ducts. It is contemplated that this apparatus may be utilized to deliver drugs for a variety of purposes to localized areas of vessels and glands. For example, it may be desirable to deliver cancer-fighting drugs to tumorous areas in this manner.

BRIEF DESCRIPTION OF THE DRAWINGS

FIG. 1 is a view of an intravascular catheter assembly in accordance with the principles of the present invention, and showing an expandable, porous membrane at the distal end of the assembly positioned in an occluded blood vessel.

FIG. 2 is an enlarged partial sectional view of the distal end of the assembly shown in FIG. 1, particularly showing an endoskeletal cage-type expandable frame in its radially contracted position.

FIG. 3 is a partial sectional view similar to FIG. 2, except that the frame is in its full dilation or expanded condition.

FIG. 4 is an enlarged sectional view of the distal end of the catheter assembly of FIG. 1, particularly showing the path of flow of the drug-containing liquid through the porous membrane and onto the stenotic region of the blood vessel.

FIG. 5 is an enlarged partial sectional view of an alternative embodiment to the distal end shown in FIGS. 2-4, particularly showing an expandable, porous outer membrane over a slotted, semi-rigid expansion element.

FIG. 6 is an elevational view of the expansion element shown in FIG. 5.

FIG. 7 is an elevational view similar to FIG. 5, except that the membrane is shown in its expanded position.

FIG. 8 is a view similar to FIG. 6, except that the expansion element is shown in its expanded position.

FIG. 9 is an elevational view of an alternative embodiment, particularly showing the expandable outer membrane bonded to a double expansion element in its expanded position.

FIG. 10 is an elevational partial sectional view of an alternative embodiment, particularly showing the outer membrane attached to an "accordion" type expansion element.

FIG. 11 is an elevational view similar to FIG. 10, except that the accordion element is in its expanded position.

FIG. 11A is an enlarged sectional view, taken along line 11A—11A in FIG. 10.

FIG. 12 is an exploded elevational view of an alternative embodiment, particularly showing means for hydraulically expanding the outer membrane.

FIG. 13 is an end view of the manifold shown in FIG. 12.

FIG. 14 is a view similar to FIG. 12, except that both the manifold and the outer membrane are shown in their expanded positions.

FIG. 15 is an end view of the manifold shown in FIG. 14.

FIG. 16 is an enlarged, assembled, partial sectional view of FIG. 12.

FIG. 17 is an enlarged, assembled, partial sectional view of FIG. 14.

DESCRIPTION OF THE PREFERRED EMBODIMENT

Referring now to the drawings, and in particular to FIG. 1, there is shown an intravascular, drug delivery dilation catheter assembly 18, which comprises a proximal end 20, an elongated catheter tube 22, and a distal end 24 that is shown inserted into a blood vessel 26 adjacent stenotic lesion 28. Elongated catheter tube 22 is adapted to receive a flexible guide wire 30. A smooth rounded plug 31, preferably formed of a radiopaque material, is provided at the distal tip of guide wire 30. Proximal end 20 includes a manipulator 32, which includes a housing 34, an internally threaded cap member 36, a torquing member 38, and an optional drug drip port 40. A two-arm adaptor 2 is threadedly secured to manipulator 32 and includes an infusion port 44 for the introduction of drug into assembly 18. A preferred drug is colchicine, carried by microparticles of a physiological-compatible, biodegradable polymer, such as polylactide or a polyanhydride, for sustained release of drug at the affected site for injection under pressure into the arterial wall in the region of the restenosis. Other drugs such as heparin may also be used. These sustained release drugs and the delivery method are disclosed in a copending U.S. patent application entitled COMPOSITION AND METHOD FOR DELIVERY OF DRUGS, Ser. No. 07/662,194, filed on Feb. 28, 1991, which disclosure is incorporated herein by reference.

Referring to FIGS. 2 and 3, there is shown an expandable, porous outer balloon or membrane 46 having a pattern of micro-apertures 48 therein. For purposes of clarity in this application, membrane 46 will be referred to in all embodiments described hereinafter. However, it is recognized that the dimensions of the membrane and the pattern of apertures therein may vary as needed for each individual embodiment. Preferably, there are a plurality of equally spaced apertures 48 having a density of 10–200/cm$^2$ expanded surface area. Each aperture 48 preferably has a diameter ranging between 25 and 75 microns. The proximal end of membrane 46 is attached to catheter tube 22 and includes an annular space (not shown) for infusion thereof. The distal end of membrane 46 is attached to a slidable collar 52. Membrane 46 is axially supported and expanded by an endoskeletal frame comprising an expandable frame in the form of cage 54 that is formed from a plurality of spirally arranged wires 56, preferably made from stainless steel, having a diameter of about 0.001 to about 0.005 inch. The number of wires forming cage 54 is typically 4 to 20. The proximal ends of wires 56 are fixed to the inner wall 58 of catheter tube 22. The distal end of wires 20 are bonded to collar 52 in a suitable manner, such as by welding, soldering or brazing. In addition, wires 56 are in contact with the inner surface 47 of membrane 46 so that any radial expansion and contraction of wires 56 causes corresponding radial expansion and contraction of membrane 46.

In order to expand membrane 46 from its radially contracted position shown in FIG. 2 to its radially expanded position shown in FIG. 3, cap 36 is rotated to cause longitudinal movement of an externally threaded element (not shown) that is rotatably mounted about torquing member 38 and whose threads engage the internal threads of cap 36. Torquing member 38, which is attached to guide wire 30, is thus longitudinally moved to longitudinally move guide wire 30. Proximal movement of guide wire 30 will move collar 52 toward cage 54 to reduce the axial distance between the ends of cage 54, thereby radially expanding the cage, as shown in FIG. 3. Likewise, distal movement of guide wire 30 will move collar 52 away from cage 54 to increase the axial distance between the ends of cage 54, thereby radially contracting cage 54, as shown in FIG. 2. It is noted that the endoskeletal frame described above may be biased in a radially contracted position or a radially expanded position. Further details of this mechanism are found in U.S. Pat. No. 5,002,560, issued to Machold, et al., which disclosure is incorporated herein by reference.

As shown in FIG. 4, cage 54 is radially expanded, thereby radially expanding membrane 46. Cage 54 is expanded until the outer surface of membrane 46 engages lesion 28. In this position, micro-apertures 48 provide the channels for fluid communication between the interior of membrane 46 and lesion 28. Once membrane 46 is expanded, a drug-containing liquid, such as heparin, is introduced through infusion port 44 and into the lumen 23 of tube 22. The liquid then flows under pressure into membrane 46, out through apertures 48, and onto or into lesion 28, as indicated by the arrows in FIG. 4. After applying the drug, cap member 36 is rotated to move guide wire 30, thus moving collar 52 back toward its original position shown in FIG. 2, thereby again radially contracting cage 54 to permit removal of the catheter from the patient.

Referring to FIGS. 5–8, an alternative embodiment to balloon assembly 24 is balloon assembly 60, wherein the distal end of catheter body 22 forms the endoskeletal frame, which is an expandable tubular frame member 62 having a plurality of slots 64 therein. Although frame member 62 is shown having four slots, each spaced about ninety degrees apart about the circumference of membrane 46, other slot configurations are possible. Slots 64 form ribs 65, which radially expand and retract. Guide wire 30 includes a pull stop 66 at the proximal end of frame member 62 for constricting the axial length thereof. Tubular frame member 62 is attached to guide wire 30 at pull stop 66. In operation, guide wire 30 is retracted, thereby forcing pull stop 66 toward frame member 62. As its axial length is constricted, ribs 65 of frame member 62 radially expands, in a manner similar to a conventional molly bolt, to its expanded position shown in FIG. 8, thereby expanding the portion of membrane 46 overlying ribs 65, as shown in FIG. 7. After expansion, the liquid drug is introduced into infusion port 44 for delivery of drug, as described above. The liquid flows under pressure through tube expanded slots 64 in frame member 62 and through micro-apertures 48 in membrane 46.

A modification to this embodiment is shown in FIG. 9, wherein a balloon assembly 68 is shown and includes an expandable tubular frame member 70 including therein four circumferentially spaced slots 72 and four circumferentially spaced slots 74 that are axially spaced from slots 72. Slots 72 and 74 form ribs 73 and 75, respectively, which expand and contract in a manner similar to a double molly bolt "in series". Membrane 46 is bonded to ribs 73 and 75. As the axial length of balloon assembly 68 is constricted by retracting guide wire 30, ribs 73 and 75 are expanded to expand membrane 46 to its position shown in FIG. 9. Preferably, apertures 48 in membrane 46 are located axially between ribs 73 and 75.

Another alternative embodiment of the balloon assembly 76 is shown in FIGS. 10-11A. More particularly, the distal end of guide wire 30 includes a threaded portion 77 that is threadedly secured to a spider 78, having radially extending arms 80 and 81, as shown in FIG. 11A. Arms 80 and 81 are bonded to inner surface 47 of pleated membrane 46. The end of threaded portion 77 is rotatably attached to disc 82 by rivet 84. The outer circumference of disc 82 is bonded to inner surface 47 of membrane 46. Upon retracting wire 30 to expand assembly 76, disc 82 is moved proximally to expand membrane 46 in an accordion-like fashion, resulting in a plurality of pleats 86 being formed, which are adapted to engage lesion 28. Apertures 48 are located preferably in the radially outer peaks of pleats 86 to deliver liquid drug from the interior 23 of membrane 46 directly to the lesion surface.

Referring now to FIGS. 12-17, yet another alternative embodiment is shown. This embodiment is different from the previous embodiments in that it utilizes hydraulic pressure to expand the porous membrane, whereas the previous embodiments utilize mechanical means for expanding and contracting the membrane. In particular, an expandable manifold element 88 is coextensive with tube 22 and includes a semi-rigid central tube 91, which functions as the guide wire, and a plurality of flexible and collapsible branched drug delivery ducts 92. As shown in FIGS. 12 and 14, membrane 46 in this embodiment differs from earlier described embodiments in that micro-apertures 48 are not in communication with the interior of membrane 46. As shown in FIG. 16, the ends 94 of ducts 92 include an outer circumferential surface 96 that is bonded to inner wall surface 47 of membrane 46 such that ducts 92 are in fluid communication with apertures 48.

In order to expand membrane 46, a working fluid, which is preferably a liquid, is introduced into tube 22, which is in fluid communication with membrane 46. As the walls of membrane 46 expand, ducts 92 expand from their collapsed positions shown in FIGS. 12 and 16 to their radially expanded positions shown in FIGS. 14 and 17. After the walls of membrane 46 are expanded into contact with the vessel wall, liquid drug is delivered through tube 90, into branched ducts 92 and out through apertures 48. After delivery of the drug, membrane 46 is radially contracted by withdrawing the working liquid from the membrane so that membrane 46 and passages 92 return to their collapsed positions for removal of the catheter from the vessel. Ducts 92 may be resiliently biased toward their collapsed position.

It is recognized that other embodiments are possible for expanding the membrane into contact with the localized area of the vessel independent of causing drug delivery to the localized area, and such other embodiments are considered to fall within the scope of the present invention.

It will be appreciated that the foregoing is presented by way of illustration only, and not by way of any limitation, and that various alternatives and modifications may be made to the illustrated embodiment without departing from the spirit and scope of the invention.

What is claimed is:

1. A method applying a drug to a localized area on the inner wall of a tubular body vessel comprising the steps of:
   providing expandable, porous outer membrane;
   inserting membrane into the vessel adjacent the localized area;
   expanding the membrane into contact with the localized area of the vessel; and
   after the step of expansion, causing a drug-containing liquid to flow under pressure through pores in the expanded membrane into contact with the localized area of the vessel;
   wherein the step of expanding the membrane occurs independently of the step of causing the drug-containing liquid to flow through the membrane.

2. The method of claim 1, including the step of pumping the drug-containing liquid through a tube and to the expanded membrane to thereby pressurize the membrane with the liquid and cause the liquid to flow through the pores of the membrane.

3. The method of claim 2, wherein the step of expanding the membrane is accomplished by expanding an endoskeletal frame within the membrane, the frame exerting mechanical force on the membrane to expand the membrane.

4. The method of claim 1, wherein the step of expanding the membrane is accomplished by expanding an endoskeletal frame within the membrane, the frame exerting mechanical force on the membrane to expand the membrane.

5. The method of claim 1, wherein the step of expansion comprises pressurizing the membrane with a working fluid that is segregated from the drug-containing liquid.

6. The method of claim 1, wherein the drug is carried by microparticles of a physiologically-compatible, biodegradable polymer.

7. A method of applying a drug to a localized area on the inner wall of a tubular body vessel comprising the steps of:
   providing an expandable, porous outer membrane;
   inserting the membrane into the vessel adjacent the localized area;
   expanding the membrane into contact with the localized area of the vessel; and
   causing a drug-containing liquid to flow under pressure into the membrane and through the pores in the membrane into contact with the localized area of the vessel;
   the step of expanding the membrane occurring independently of the flow of pressurized drug-containing liquid into the membrane and through the pores in the membrane.

8. The method of claim 7, wherein the step of expanding the membrane is accomplished by expanding an endoskeletal frame within the membrane, the frame exerting mechanical force on the membrane to expand the membrane.

9. A method of treating a stenotic atherosclerotic lesion on the interior wall of a blood vessel comprising the steps of:
providing an expandable, porous outer membrane;
inserting the membrane into the blood vessel adjacent the lesion;
expanding the membrane into contact with the lesion; and
after the step of expansion, causing a drug-containing liquid to flow under pressure through pores in the expanded membrane into contact with the lesion;
wherein the step of expanding the membrane occurs independently of the flow of the drug-containing liquid through the membrane.

10. The method of claim 9, including the step of pumping the drug-containing liquid through a tube into the expanded membrane to thereby pressurize the membrane with the liquid and cause the liquid to flow through the pores of the membrane.

11. The method of claim 10, wherein the step of expanding the membrane is accomplished by expanding an endoskeletal frame within the membrane, the frame exerting mechanical force on the membrane to expand the membrane.

12. The method of claim 9, wherein the step of expanding the membrane is accomplished by expanding an endoskeletal frame within the membrane, the frame exerting mechanical force on the membrane to expand the membrane.

13. The method of claim 9, wherein the step of expansion comprises pressurizing the membrane with a working fluid that is segregated from the drug-containing liquid.

14. The method of claim 9, wherein the drug is carried by microparticles of a physiologically-compatible, biodegradable polymer.

15. A method of treating a stenotic atherosclerotic lesion on the interior wall of a blood vessel comprising the steps of:
providing an expandable, porous outer membrane;
inserting the membrane into the blood vessel adjacent the lesion;
expanding the membrane into contact with the lesion; and
causing a drug-containing liquid to flow under pressure into the membrane and through pores in the membrane into contact with the lesion, the step of expansion occurring independently of the flow of pressurized drug-containing liquid into the membrane and through the pores in the membrane.

16. The method of claim 15, wherein the step of expanding the membrane is accomplished by expanding an endoskeletal frame within the membrane, the frame exerting mechanical force on the membrane to expand the membrane.

17. Apparatus for applying a drug to a localized area of a tubular body vessel comprising:
an expandable, porous outer membrane;
an elongate flexible tube connected to said membrane;
means for pumping a drug-containing liquid through said tube into said membrane and through pores in said membrane; and
means for mechanically expanding the membrane into contact with the vessel independently of the pumping of the liquid into and through said membrane.

18. The apparatus of claim 17, wherein said means for expanding comprises an endoskeletal frame within said membrane and means for expanding said frame to exert mechanical force on said membrane to thereby expand said membrane.

19. The apparatus of claim 18, including means for contracting said frame.

20. The apparatus of claim 18, wherein said endoskeletal frame comprises a wire mesh cage, and said means for expanding comprises a retractable wire connected to said mesh cage to expand the mesh cage when the wire is retracted.

21. The apparatus of claim 20, wherein said membrane is bonded to said cage.

22. The apparatus of claim 18, wherein said endoskeletal frame is an expandable stent.

23. The apparatus of claim 18, wherein said endoskeletal frame comprises a tubular frame member having a plurality of slots therein forming a plurality of ribs, and said means for expanding comprises a retractable wire connected to the tubular frame member for causing said ribs to expand radially when the wire is retracted.

24. The apparatus of claim 23, wherein said membrane is bonded said ribs.

25. The apparatus of claim 23, wherein said tubular frame member includes a second plurality of slots to form a second plurality of ribs spaced axially from the first mentioned plurality of ribs, wherein said wire expands said second plurality of ribs.

26. The apparatus of claim 25, wherein said porous membrane extends between said first mentioned and second plurality of ribs.

27. The apparatus of claim 24, wherein said tubular frame member extends axially through said flexible tube into said membrane at a proximal end of said membrane, said wire being attached to said tubular frame member at a distal position thereof, and said ribs being disposed intermediate the attachment position of said wire and the proximal end of the membrane.

28. The apparatus of claim 17, wherein said membrane is pleated and said means for expanding comprises means for contracting said membrane axially to thereby cause the pleated membrane to expand radially.

29. The apparatus of claim 28, including pores in said pleats at radially outer peaks thereof.

30. The apparatus of claim 17, including ducts within said membrane connected to said pores, said ducts being in communication with said means for pumping, and wherein said means for expanding comprises means for hydraulically expanding said membrane.

31. The apparatus of claim 30, wherein said means for hydraulically expanding comprises a second flexible tube coextensive with said first mentioned flexible tube and being in communication with said membrane, and means for pumping fluid through said second tube into said membrane to expand said membrane 32. The apparatus of claim 17, wherein said flexible tube is in fluid communication with said membrane.

33. The apparatus of claim 32, wherein said means for expanding comprises an endoskeletal frame within said membrane and means for expanding said frame to exert mechanical force on said membrane to thereby expand said membrane.

34. The apparatus of claim 33, including means for contracting said frame.

35. The apparatus of claim 17, wherein the drug is carried by microparticles of a physiologically-compatible, biodegradable polymer.

* * * * *